United States Patent [19]

Scheid

[11] Patent Number: 5,124,654
[45] Date of Patent: Jun. 23, 1992

[54] INTEGRATED DEVICES FOR THE DETERMINATION OF THE ALCOHOL CONTENT AND/OR THE CALORIFIC VALUE OF FUELS

[75] Inventor: Ernst Scheid, Aachen, Fed. Rep. of Germany

[73] Assignee: FEV Motorentechnik GmbH & Co. KG, Aachen, Fed. Rep. of Germany

[21] Appl. No.: 446,728

[22] Filed: Dec. 6, 1989

[30] Foreign Application Priority Data

Dec. 22, 1988 [DE] Fed. Rep. of Germany ....... 3843177

[51] Int. Cl.$^5$ ............................................. G01N 27/22
[52] U.S. Cl. ................................... 324/658; 324/663; 324/446; 123/494
[58] Field of Search ............... 324/658, 663, 672, 674, 324/681, 690, 446, 448, 450, 698; 73/116; 123/494

[56] References Cited

U.S. PATENT DOCUMENTS

| | | | |
|---|---|---|---|
| 4,470,300 | 9/1984 | Kobayashi | 324/677 X |
| 4,599,888 | 7/1986 | Hufton | 324/690 X |
| 4,767,995 | 8/1988 | Berry, Jr. | 324/448 X |
| 4,905,655 | 3/1990 | Maekawa | 73/116 X |
| 4,939,467 | 7/1990 | Noglami et al. | 324/663 |
| 4,939,468 | 7/1990 | Takeuchi | 324/663 X |

FOREIGN PATENT DOCUMENTS 0080848  3/1989  Japan ................................. 324/663

OTHER PUBLICATIONS

Proceedings of the Fourth International Symposium on Alcohol Fuels Technology, Sao Paulo, Brazil, Oct. 5, 1980, pp. 379-383.

*Primary Examiner*—Kenneth A. Wieder
*Attorney, Agent, or Firm*—Watson, Cole, Grindle & Watson

[57] ABSTRACT

A device is provided for improving the measuring accuracy of a process for determining the alcohol content and/or the calorific value of fuels by measuring the electrically measurable qualities of fuel. At least one component of the fuel system of an engine is used with a counterelectrode for the capacitive dielectric measurement of the fuel. At the same time, it is suitable to also use a component of the fuel system with respect to a counterelectrode for the measurement of the conductivity of the fuel. The same counterelectrode can be used for the dielectric measurement and for the measurement of conductivity of the fuel.

14 Claims, 3 Drawing Sheets

INTEGRATED DEVICES FOR THE DETERMINATION OF THE ALCOHOL CONTENT AND/OR THE CALORIFIC VALUE OF FUELS

The present application relates to commonly owned U.S. patent applications Ser. No. 391,248, filed Aug. 9, 1987 and Ser. No. 329,839, filed Mar. 23, 1989, concurrently filed applications Ser. Nos. 446,726, 446,781 and 446,780, and U.S. application Ser. No. 535,062 filed Jun. 8, 1990.

BACKGROUND OF THE INVENTION

The present invention relates to a method and device for the determination of the alcohol content and/or the calorific value of fuels by measuring electrically measurable quantities of fuel.

In light of diminishing fossil energy reserves of fuels obtained from crude oil and stricter environmental protection requirements, increasing amounts of methyl or ethyl alcohol are being added to these fuels. Thus, any arbitrary refueling should be possible both with pure fuels and mixed fuels. When the alcohol content is higher, it is necessary to know the blending ratio in order to obtain optimal performance from the fuel-burning engine and to enable a precise proportioning of fuel adjusted to the operating conditions. The continuous determination of the alcohol content in the fuel fed into the fuel-burning engine in operation presents special problems for automobile engines in which any possible blend may be present by arbitrary refueling with various types of fuel.

The known optical processes are hardly suitable for this purpose since they often utilize interface effects to determine the refraction index, from which the alcohol content can be inferred. In addition to the difficulty of using these processes in automobile engines, another drawback of this process is that the mix to be observed must have a high homogeneity, especially at the interface. The required precision has not been achieved with this process.

Therefore, it has been proposed that the alcohol content in fuels be determined by means of a dielectric analysis. Such a process would solve the problem concerning measurement of the interface effects since measurement is done volumetrically. On the other hand, the conductance of the mixture significantly affects the volumetric dielectric analysis (cross sensitivity). Since the conductance is a function primarily of the pollutants or the water content, such a measuring process leads to useless results.

The possibility of determining the alcohol content of fuels by means of dielectric measurements is explored in the document "Proceedings of the Fourth International Symposium on Alcohol Fuels Technology," Sao Paulo, Brazil of Oct. 5, 1980. However, the process was rejected since the influences of temperature and conductance (induced by water content or other pollutants in the fuel) prevented a reliable measurement suitable for fuel-burning engines from being obtained.

Therefore, it is an object of the present invention to provide a process of the aforementioned kind which permits a precise and reliable determination of the alcohol content and/or calorific value in fuels, in particular for application in automobile engines.

Other objects and advantages will become apparent from the specification and drawings which follow.

SUMMARY OF THE INVENTION

The foregoing and additional objects are obtained by a process according to the present invention in which at least one component of the fuel system is used, with respect to a counterelectrode, for the capacitive dielectric measurement of the fuel or dielectric. At the same time, it is suitable to also use a component of the fuel system, with respect to the counterelectrode, to measure the conductance of the fuel in order to rule out cross influences which are caused primarily by the water content and other pollutants or admixtures of the fuel.

Since a component of the fuel system is used for the capacitive dielectric measurement of the fuel, relatively large capacitor areas are obtained which permit a significantly more precise dielectric measurement than separate measuring systems of prior art. At the same time the cost of a separate measuring system is saved. Other advantages include space savings and better protection of the measuring system both mechanically and with respect to electric noise fields.

An embodiment of the invention provides that the same counterelectrode is used for the dielectric measurement and for the measurement of the conductance of the fuel.

DETAILED DESCRIPTION OF THE PREFERRED EMBODIMENTS

Figure 1:
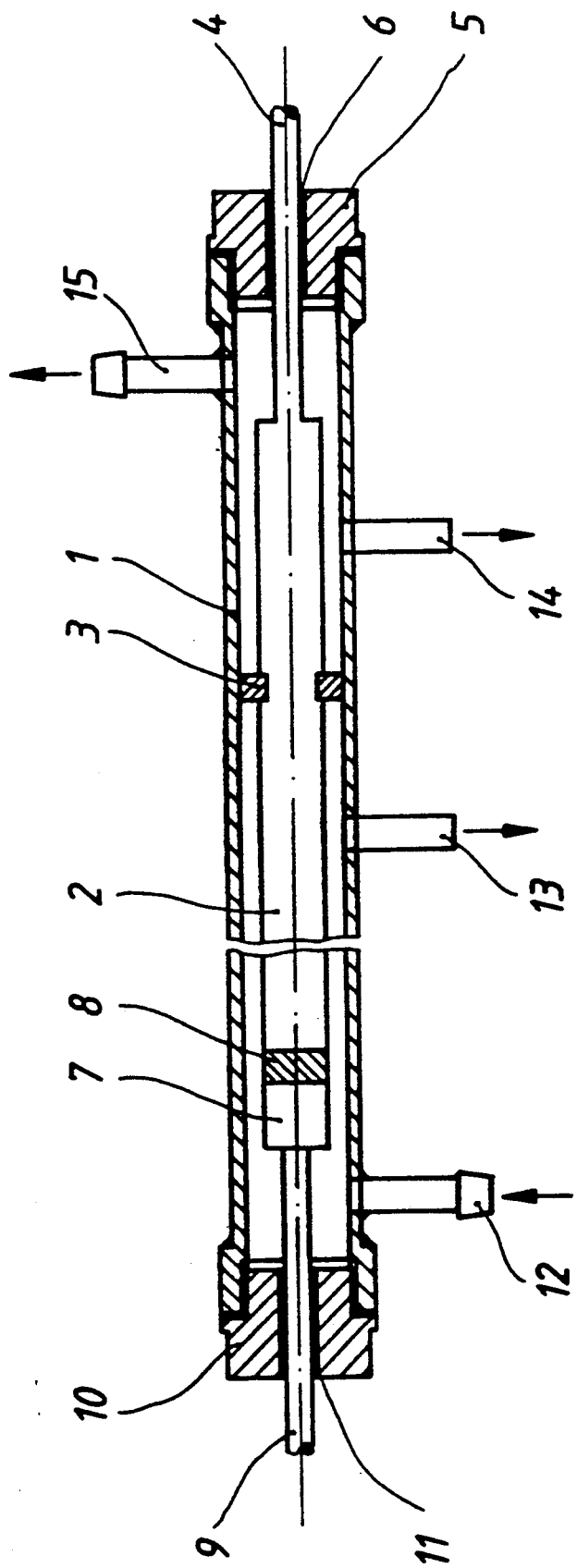
FIG. 1 is a longitudinal view of the present invention integrated with a fuel distributing pipe, arranged directly upstream of the fuel injection valves of a fuel-burning engine.

The present invention will now be described in greater detail with reference to the accompanying drawings. Referring to FIG. 1, an embodiment of a measuring system for conducting the process of capacitive measurement of the dielectric constants is shown. The measuring system comprising in essence a fuel distributing pipe 1 which is arranged directly upstream of the fuel injection valves of an injection fuel-burning engine and which, as a part of the fuel system, forms the outer electrode of a capacitor for measuring the dielectric constants of the fuel. Within distributing pipe 1, there is a cylindrical counterelectrode 2 made of electrically conductive material, which is held by means of a spacer 3 at a constant distance from the distributing pipe 1.

An electric connection 4 of the counterelectrode 2 for measuring the dielectric constants is guided to the outside by means of a screw coupling 5 with insulation 6 and can be connected directly to an electronic measuring circuit (not illustrated).

There is also an electrode 7 for measuring the conductivity of the fuel, which, as in the case of the first electrode, assumes the function of a counterelectrode to the fuel distributing pipe 1. In the embodiment shown the electrode 7 is also designed cylindrically as in the case of the counterelectrode 2, and the electrode 7 is separated from the counterelectrode by means of an insulator 8. Its dimensions can in general by significantly smaller than those of the counterelectrode 2.

As in the case of the counterelectrode 2, the electric connection 9 of the electrode 7 for measuring the conductivity can in a similar manner be guided to the outside by means of a screw coupling 10 with insulation 11 and be connected to the measuring circuit, whereby the calorific value of the fuel is determined. Thus, the fuel distributing pipe 1 serves as the common electrode for both the dielectric measurement and the conductivity measurement.

The alcohol content and the calorific value of the fuel may then be determined by the methods disclosed in commonly owned U.S. patent application Ser. No. 329,839, filed Mar. 28, 1989.

The fuel flows at fuel connection 12 into the fuel distributing pipe 1 and a portion of the fuel exits at line connections 13 and 14 to the fuel injection valves (not illustrated). The remaining fuel flows to the fuel return 15.

Figure 2:
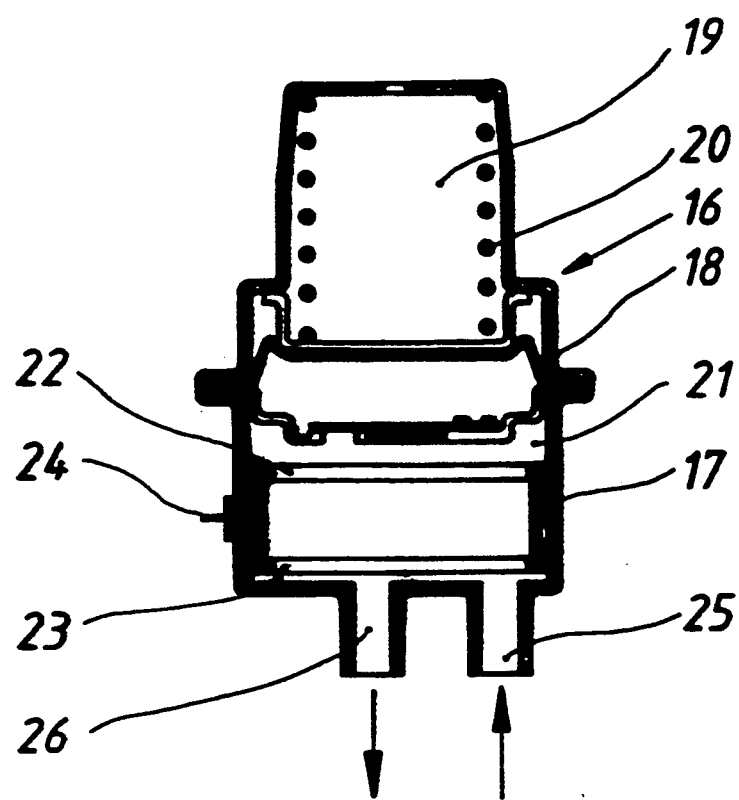
FIG. 2 is a simplified and cutaway view of the present invention in a spring energy store of a fuel system.

FIG. 2 shows another embodiment of the process for the capacitive measurement of the dielectric constants of the fuel. Here, as a component of the fuel system, a spring energy store 16 is equipped with an internal electrode 17 to mounted by means of mountings 22 and 23 and insulated with respect to the conductive housing. The electric connection 24 of the internal electrode 17 is guided out of the housing in an insulated manner and can be connected directly to a measuring circuit. The fuel flows over fuel entry supports 25 into the housing of the spring energy store 16 and it is further conveyed by meas of fuel outlet supports 26.

Figure 3:
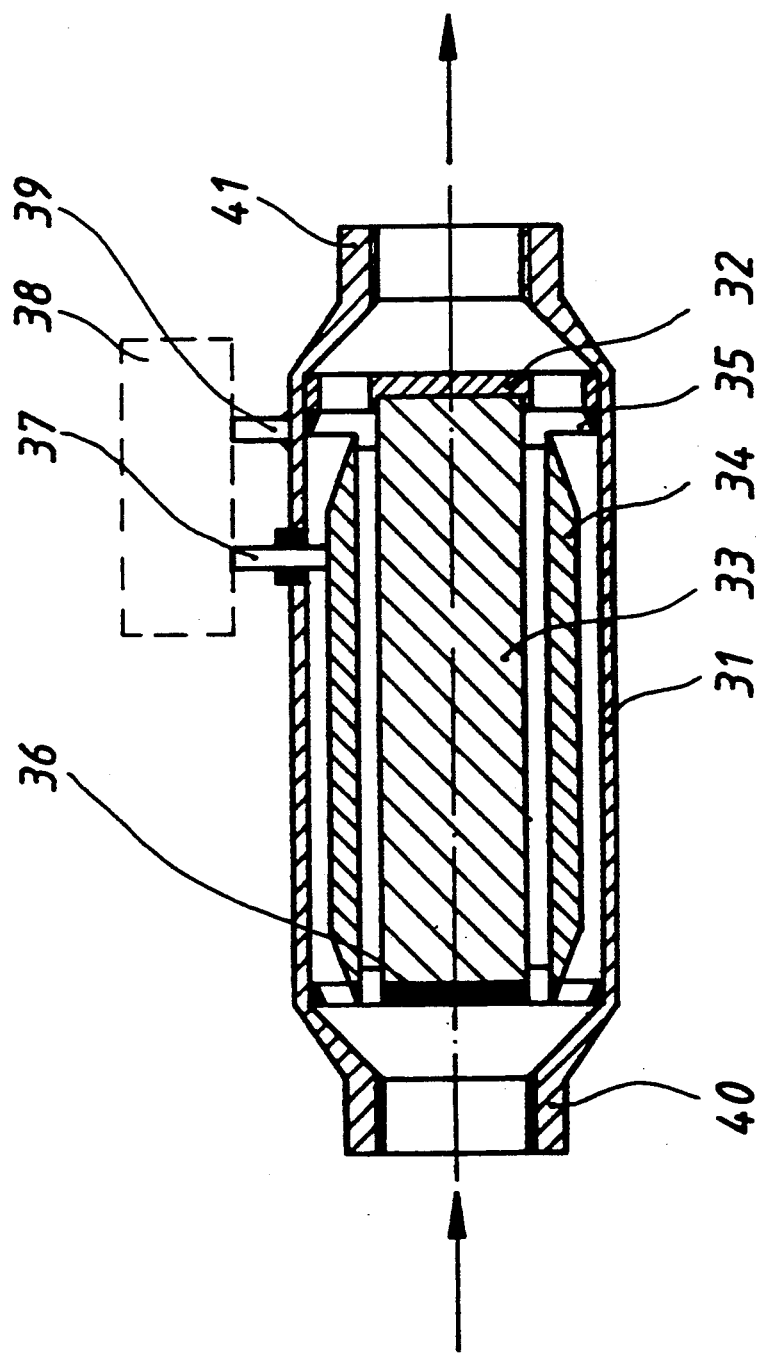
FIG. 3 is a longitudinal view of the present invention in the fuel line system of a fuel-burning engine.

As compared to the systems shown in FIGS. 1 and 2, the embodiment shown in FIG. 3 enables the design of an even larger capacitor area so that a higher capacitance and thus even better measuring accuracy can be attained. Increasing the capacitance also facilitates the design of the electronic measuring circuit.

The outer electrode 31 is a part of the fuel system, for example a pipe line, which, if necessary, can be expanded even slightly. The outer electrode 31 is connected so as to be electrically conductive to a cylindrical internal part 33 serving as an electrode by means of a spacer 32. The counterelectrode to the electrodes 31 and 33 comprises a hollow cylinder 34 which is mounted so as to be insulated in spacers 35 and 36. The hollow cylindrically electrode 34 is connected to an electronic measuring and/or analysis circuit 38 by means of an insulated connection 37. The electrodes 31 and 33 are connected to the measuring and/or analysis circuit by means of connection 39.

The fuel enters into the measuring system by means of the entry supports 40 and the fuel stream branches in the illustrated manner along both sides of the hollow cylinder 34. The fuel then exits via outlet support 41.

Of course, any suitable component of the fuel system may be utilized to define a cavity for the fuel and the inner center electrode(s). Thus, the preceding examples are only intended to be illustrative of the possible embodiments of the concept of the present invention.

As a component of the fuel system for the capacitive dielectric measurement, preferably the line system of the fuel is used and in particular a metal line. However, advantages can also be attained if an exterior electrode is arranged in a nonmetal fuel line since even in such a case a relatively large capacitor area is available. Moreover, fuel-storing parts of the fuel system are also primarily used for the capacitive dielectric measurement, e.g. the fuel tank, the pressure controller, the pressure holding valve or the spring energy store.

Many modifications and improvements will be apparent to one skilled in the art without departing from the spirit and scope of the present invention as defined by the following claims.

I claim:

1. A device for determining relative proportions of components in a multicomponent variable dielectric using a capacitance measurement, said device comprising:
   a capacitive cell for receiving a multicomponent variable dielectric, having a first electrode and a second electrode; and
   means for connecting said first electrode to a measuring circuit, whereby the relative proportions of the components of the multicomponent variable dielectric are determined by a measured capacitance of the variable dielectric, wherein
   said first electrode is an existing hollow metallic component of a flow channel which is part of a fuel system of an internal combustion engine driven vehicle; and
   said second electrode is located within and spaced from the existing hollow metallic component.

2. The device according to claim 1, wherein said cell is a fuel distributing pipe having a fuel inlet and a first fuel outlet.

3. The device according to claim 1, further comprising means for supporting said second electrode at a constant distance from the interior of said cell, whereby said second electrode and the cell interior form another capacitive cell to measure the conductivity of the variable dielectric, and means for connecting said second electrode to the measuring circuit to determine the calorific value of the dielectric.

4. The device according to claim 3, wherein said second electrode is affixed to said first electrode with an insulation located therebetween.

5. The device according to claim 1, wherein said cell and said first electrode are cylindrical.

6. The device according to claim 4, wherein said cell, said first electrode and said second electrode are cylindrical and said second electrode is affixed to an end of said cylindrical first electrode.

7. The device according to claim 6, further comprising a screw coupling secured to an end of said cylindrical cell, said connecting means for said first electrode passing through said screw coupling.

8. The device according to claim 7, further comprising another screw coupling secured to another end of said cylindrical cell, said connecting means for said second electrode passing through said another screw coupling.

9. The device according to claim 1, wherein said cell comprises a membrane defining a chamber and a spring chamber having a spring biased against the membrane, said first electrode being located within the chamber, and a fuel inlet and a fuel outlet located in the chamber.

10. The device according to claim 1, wherein said cell and said first electrode are cylinders and further comprising a hollow cylinder defining a counterelectrode mounted between said cell and said first electrode, means for connecting said counterelectrode to the measuring circuit and means for connecting said cell to the measuring circuit.

11. The device according to claim 10, wherein said cell has a fuel inlet and a fuel outlet for the dielectric.

12. A device according to claim 1, wherein said variable dielectric is a mixture of hydrocarbons and alcohol which make up a fuel mixture for internal combustion engines.

13. A device according to claim 12, wherein the proportion of alcohol is determined by a measured capacitance and conductance of the fuel mixture to achieve an improved accuracy of the measurement.

14. A device according to claim 1, wherein the relative proportions of the components are determined by a measured capacitance and conductance of the variable dielectric to achieve an improved accuracy of the measurement.

* * * * *